(12) United States Patent
Cochrum et al.

(10) Patent No.: US 7,101,862 B2
(45) Date of Patent: Sep. 5, 2006

(54) HEMOSTATIC COMPOSITIONS AND METHODS FOR CONTROLLING BLEEDING

(75) Inventors: Kent C. Cochrum, Davis, CA (US); Susan Jemtrud, San Francisco, CA (US)

(73) Assignee: Area Laboratories, LLC, West Sacramento, CA (US)

( * ) Notice: Subject to any disclaimer, the term of this patent is extended or adjusted under 35 U.S.C. 154(b) by 129 days.

(21) Appl. No.: 10/334,864

(22) Filed: Dec. 31, 2002

(65) Prior Publication Data

US 2003/0175327 A1 Sep. 18, 2003

Related U.S. Application Data

(60) Provisional application No. 60/354,917, filed on Feb. 11, 2002, provisional application No. 60/343,247, filed on Dec. 31, 2001.

(51) Int. Cl.
| | |
|---|---|
| A61K 31/729 | (2006.01) |
| A61K 31/721 | (2006.01) |
| A61K 31/718 | (2006.01) |
| A61L 15/00 | (2006.01) |

(52) U.S. Cl. .......................... 514/54; 514/57; 514/59; 514/60; 536/3; 536/56; 536/102; 536/112; 536/123.1; 536/124; 424/445; 424/422; 424/443; 424/488; 424/499

(58) Field of Classification Search .................. 514/54, 514/57, 59, 60; 536/3, 56, 102, 112, 123.1, 536/124; 424/445, 422, 443, 488, 499
See application file for complete search history.

(56) References Cited

U.S. PATENT DOCUMENTS

| | | | |
|---|---|---|---|
| 2,387,642 A | 10/1945 | Calhoun | |
| 3,206,361 A | 9/1965 | Shelley et al. | |
| 3,507,851 A | 4/1970 | Ghetie et al. | |
| 3,671,280 A * | 6/1972 | Smith | 524/5 |
| 3,810,473 A | 5/1974 | Cruz, Jr. et al. | |
| 3,959,079 A | 5/1976 | Mareschi et al. | |
| 3,959,080 A | 5/1976 | Orth et al. | |
| 4,137,399 A | 1/1979 | Hülsmann et al. | |
| 4,175,183 A | 11/1979 | Ayers | |
| 4,298,598 A | 11/1981 | Schwarz et al. | |
| 4,362,567 A | 12/1982 | Schwarz et al. | |
| 4,377,572 A | 3/1983 | Schwarz et al. | |
| 4,405,324 A | 9/1983 | Cruz, Jr. | |
| 4,414,976 A | 11/1983 | Schwarz et al. | |
| 4,427,651 A | 1/1984 | Stroetmann | |
| 4,543,410 A | 9/1985 | Cruz, Jr. | |
| 4,549,653 A | 10/1985 | Lauritzen | |
| 4,554,156 A | 11/1985 | Fischer et al. | |
| 4,556,056 A | 12/1985 | Fischer et al. | |
| 4,599,209 A | 7/1986 | Dautzenberg et al. | |
| 4,616,644 A | 10/1986 | Saferstein et al. | |
| 4,617,326 A | 10/1986 | Björnberg et al. | |
| 4,626,253 A | 12/1986 | Broadnax, Jr. | |
| 4,640,778 A | 2/1987 | Blomback et al. | |
| 4,665,164 A | 5/1987 | Pernemalm et al. | |
| 4,696,286 A | 9/1987 | Cochrum | |
| 4,738,849 A | 4/1988 | Sawyer | |
| 4,749,689 A | 6/1988 | Miyata et al. | |
| 4,777,249 A | 10/1988 | Bridgeford | |
| 4,793,336 A | 12/1988 | Wang | |
| 4,973,683 A | 11/1990 | Lindgren | |
| 5,015,476 A | 5/1991 | Cochrum et al. | |
| 5,035,893 A | 7/1991 | Shioya et al. | |
| 5,059,654 A | 10/1991 | Hou et al. | |
| 5,064,652 A | 11/1991 | Bay | |
| 5,064,950 A | 11/1991 | Okuma et al. | |
| 5,076,265 A | 12/1991 | Wokalek | |
| 5,077,210 A | 12/1991 | Eigler et al. | |
| 5,081,041 A * | 1/1992 | Yafuso et al. | 436/68 |
| 5,098,417 A | 3/1992 | Yamazaki et al. | |
| 5,144,016 A | 9/1992 | Skjak-Braek et al. | |
| 5,185,001 A | 2/1993 | Galanakas | |
| 5,196,190 A | 3/1993 | Nangia et al. | |
| 5,225,047 A | 7/1993 | Graef et al. | |
| 5,279,955 A | 1/1994 | Pegg et al. | |
| 5,295,997 A | 3/1994 | Vuillaume et al. | |
| 5,330,974 A | 7/1994 | Pines et al. | |
| 5,346,485 A | 9/1994 | Yarbrough et al. | |
| 5,393,304 A | 2/1995 | Vuillaume et al. | |
| 5,406,671 A | 4/1995 | Green | |
| 5,429,821 A | 7/1995 | Dorian et al. | |
| 5,470,576 A * | 11/1995 | Patel | 424/445 |
| 5,470,731 A | 11/1995 | Cochrum | |

(Continued)

FOREIGN PATENT DOCUMENTS

GB 854715 11/1960

(Continued)

OTHER PUBLICATIONS

Flodin, "Chapter 2: The preparation of dextran gels," *Dextran Gels and Their Applications in Gel Filtration*, Pharmacia, Uppsala, Sweden, 1962, pp. 14-26.

(Continued)

*Primary Examiner*—James O. Wilson
*Assistant Examiner*—Devesh Khare
(74) *Attorney, Agent, or Firm*—Fish & Richardson P.C., P.A.

(57) ABSTRACT

The invention provides hemostatic compositions useful to promote hemostasis at active bleeding wound sites. The hemostatic compositions typically include an article containing cellulose, e.g., cotton gauze, and a polysaccharide covalently linked to the cellulose, or a polysaccharide ionically cross-linked and in association with the article. Methods of making and using the hemostatic compositions are also provided.

14 Claims, No Drawings

U.S. PATENT DOCUMENTS

| | | | |
|---|---|---|---|
| 5,502,042 A | 3/1996 | Gruskin et al. | |
| 5,510,102 A | 4/1996 | Cochrum | |
| 5,514,377 A | 5/1996 | Cochrum et al. | |
| 5,521,079 A | 5/1996 | Dorian et al. | |
| 5,531,997 A | 7/1996 | Cochrum | |
| 5,575,997 A | 11/1996 | Leung et al. | |
| 5,578,314 A | 11/1996 | Cochrum et al. | |
| 5,584,827 A | 12/1996 | Korteweg et al. | |
| 5,614,204 A | 3/1997 | Cochrum | |
| 5,624,669 A | 4/1997 | Leung et al. | |
| 5,639,467 A | 6/1997 | Dorian et al. | |
| 5,643,192 A | 7/1997 | Hirsch et al. | |
| 5,643,594 A | 7/1997 | Dorian et al. | |
| 5,643,596 A | 7/1997 | Pruss et al. | |
| 5,645,849 A | 7/1997 | Pruss et al. | |
| 5,656,468 A | 8/1997 | Dorian et al. | |
| 5,658,592 A | 8/1997 | Tanihara et al. | |
| 5,667,501 A | 9/1997 | Fowler et al. | |
| 5,679,372 A | 10/1997 | Shimuzu et al. | |
| 5,681,579 A | 10/1997 | Freeman | |
| 5,690,610 A | 11/1997 | Ito et al. | |
| 5,693,514 A | 12/1997 | Dorian et al. | |
| 5,696,101 A | 12/1997 | Wu et al. | |
| 5,733,545 A | 3/1998 | Hood, III | |
| 5,739,288 A | 4/1998 | Edwardson et al. | |
| 5,750,657 A | 5/1998 | Edwardson et al. | |
| 5,756,464 A | 5/1998 | Scannon et al. | |
| 5,763,410 A | 6/1998 | Edwardson et al. | |
| 5,763,411 A | 6/1998 | Edwardson et al. | |
| 5,770,194 A | 6/1998 | Edwardson et al. | |
| 5,770,229 A | 6/1998 | Tanihara et al. | |
| 5,773,033 A | 6/1998 | Cochrum et al. | |
| 5,788,662 A | 8/1998 | Antanavich et al. | |
| 5,795,570 A | 8/1998 | Weber et al. | |
| 5,795,581 A | 8/1998 | Segalman et al. | |
| 5,800,372 A | 9/1998 | Bell et al. | |
| 5,804,213 A | 9/1998 | Rolf | |
| 5,804,428 A | 9/1998 | Edwardson et al. | |
| 5,817,381 A | 10/1998 | Chen et al. | |
| 5,834,008 A | 11/1998 | Greenspan et al. | |
| 5,844,087 A | 12/1998 | Zimmerman et al. | |
| 5,846,213 A | 12/1998 | Wan | |
| 5,855,620 A | 1/1999 | Bishopric et al. | |
| 5,856,367 A | 1/1999 | Barrows et al. | |
| 5,866,113 A | 2/1999 | Hendriks et al. | |
| 5,876,742 A * | 3/1999 | Cochrum et al. | 424/424 |
| 5,883,078 A | 3/1999 | Seelich et al. | |
| 5,902,877 A | 5/1999 | Hirai et al. | |
| 6,001,387 A | 12/1999 | Cochrum | |
| 6,054,122 A | 4/2000 | MacPhee et al. | |
| 6,056,970 A | 5/2000 | Greenawalt et al. | |
| 6,060,461 A | 5/2000 | Drake | |
| 6,117,425 A | 9/2000 | MacPhee et al. | |
| 6,121,508 A * | 9/2000 | Bischof et al. | 602/52 |
| 6,156,334 A | 12/2000 | Meyer-Ingold et al. | |
| 6,162,241 A | 12/2000 | Coury et al. | |
| 6,200,595 B1 | 3/2001 | Motoyashiki et al. | |
| 6,217,894 B1 | 4/2001 | Sawhney et al. | |
| 6,261,679 B1 | 7/2001 | Chen et al. | |
| 6,280,474 B1 | 8/2001 | Cassidy et al. | |
| 6,303,585 B1 | 10/2001 | Spiro et al. | |
| 6,391,048 B1 | 5/2002 | Ginn et al. | |
| 6,447,534 B1 | 9/2002 | Cragg et al. | |
| 6,454,787 B1 | 9/2002 | Maddalo et al. | |
| 6,486,285 B1 | 11/2002 | Fujita | |

FOREIGN PATENT DOCUMENTS

| | | | |
|---|---|---|---|
| GB | 942305 | 11/1963 | |
| GB | 974054 | 11/1964 | |
| GB | 983073 | 2/1965 | |
| GB | 1454055 | 10/1976 | |
| GB | 2 118 482 | 11/1983 | |
| GB | 2 207 865 | 10/1991 | |
| WO | WO 00/27327 | 5/2000 | |
| WO | WO 00/76533 | * 12/2000 | |
| WO | WO 01/05370 | * 1/2001 | |

OTHER PUBLICATIONS

Flodin, *Dextran Gels and Their Applications in Gel Filtration*, Pharmacia, Uppsala, Sweden, 1962, pp. 31-32.

Eloy et al., "An in vitro evaluation of the hemostatic activity of topical agents," *J. Biomed. Mater. Res.*, 1988, 22(2):149-157.

Larson, "Topical hemostatic agents for dermatologic surgery," *J. Dermatol. Surg. Oncol.*, 1988, 14(6):623-32.

Sigma-Aldrich Product Catalog for DEAE Sephadex A25, 1 page, 2002.

Alam et al., "Application of a Zeolite Hemostatic Agent Achieves 100% Survival in a Lethal Model of Complex Groin Injury in Swine," *J. Trauma*, 2004, 56:974-983.

Alam et al., "Comparative Analysis of Hemostatic Agents in a Swine Model of Lethal Groin Injury," *J. Trauma*, 2003, 54:1077-1082.

CROSSEAL™ Fibrin Sealant (Human), product label, 2003, 1-17.

Ivins et al., "Traumatic Brain Injury in U.S. Army Paratroopers: Prevalence and Character," *J. Trauma*, 2003, 55:617-621.

Jan-Christer Janson et al., "The 40$^{th}$ Anniversary of Sephadex," *Downstream Thirty*, 1999, 8-10.

Jewelewicz et al., "Modified Rapid Deployment Hemostat Bandage Reduces Blood Loss and Mortality in Coagulopathic Pigs with Severe Liver Injury," *J. Trauma*, 2003, 55:275-281.

Pusateri et al., "Application of a Granular Mineral-Based Hemostatic Agent (QuickClot) to Reduce Blood Loss After Grade V Liver Injury in Swine," *J. Trauma*, 2004, 57:555-562.

Pusateri et al., "Advanced Hemostatic Dressing Development Program: Animal Model Selection Critera and Results of a Study of Nine Hemostatic Dressings in a Model of Severe Large Venous Hemorrhage and Hepatic Injury in Swine," *J. Trauma*, 2003, 55:518-526.

Sondeen et al., "Comparison of 10 Different Hemostatic Dressings in an Aortic Injury," *J. Trauma*, 2003, 54:280-285.

Tisseel VH Fibrin Sealant Two-Component Fibrin Sealant, Vapor Heated, Kit, product label, 2003, 3 pages.

Vournakis et al., "Isolation, Purification, and Characterization of Poly-N-Acetyl Glucosamine Use as a Hemostatic Agent," *J. Trauma*, 2004, 57:S2-S6.

Vournakis et al., "The RDH Bandage: Hemostasis and Survival in a Lethal Aortotomy Hemorrhage Model," *J. Surg. Res.*, 2003, 113:1-5.

Definition of "gauze", *The American Heritage Dictionary of the English Language*, Third Edition, Houghton Mifflin Company, Boston, 1992, p. 752.

* cited by examiner

HEMOSTATIC COMPOSITIONS AND METHODS FOR CONTROLLING BLEEDING

RELATED APPLICATION DATA

This application claims priority from U.S. Provisional Patent Application No. 60/343,247, filed Dec. 31, 2001, and from U.S. Provisional Patent Application No. 60/354,917, filed Feb. 11, 2002.

TECHNICAL FIELD

This invention relates to hemostatic compositions and methods employing the same, and more particularly to hemostatic compositions useful for controlling bleeding at active bleeding wound sites.

BACKGROUND

Wounds are generally classified as acute or chronic in accordance with their healing tendencies. Acute wounds, typically those received as a result of surgery or trauma, usually heal uneventfully within an expected time frame. Acute wounds include wounds such as active bleeding wound sites, e.g, wounds that have detectable, unclotted blood. The rapid control of topical bleeding at active bleeding wound sites is of critical importance in wound management, especially for the management of trauma, e.g., as a result of military exercises or surgery.

A conventional method of controlling bleeding at active bleeding wound sites, such as an external hemorrhage or a surgical wound, advocates the use of cotton gauze pads capable of absorbing 250 ml of blood. Cotton pads are considered passive, however, because of their inability to initiate or accelerate blood clotting. Other formulations have been reported to promote hemostasis and are described in U.S. Pat. Nos. 6,454,787; 6,060,461; 5,196,190; 5,667,501; 4,793,336; 5,679,372; 5,098,417; and 4,405,324. A hemostatic composition capable of accelerating the coagulation cascade to form a thrombus would be useful.

SUMMARY

Accordingly, the invention relates to hemostatic compositions and methods for making and using the same in order to promote hemostasis at active bleeding wound sites. The present compositions typically include an article which contains cellulose, e.g., cotton gauze, and a polysaccharide covalently linked to the cellulose. In other embodiments, a polysaccharide is ionically cross-linked and in association with an article comprising cellulose. Hemostatic compositions can include additional polysaccharides covalently linked to either or both of the cellulose and the first polysaccharide or physically trapped by a network formed by the covalent linking or ionic cross-linking of the first polysaccharide.

In one aspect of the invention, a method for controlling bleeding at an active bleeding wound site of an animal is provided. The animal can be a mammal. For example, the animal can be a human, horse, bird, dog, cat, sheep, cow, or monkey. The method includes applying a hemostatic composition to the active bleeding wound site. The hemostatic composition includes an article which contains cellulose and a polysaccharide, such as dextran, starch, or alginate, covalently linked to the cellulose. If dextran is used, it may be in the form of a bead, e.g., covalently cross-linked dextran beads. The molecular weight of the dextran can range from about 10,000 to about 2,000,000 Daltons, or from about 20,000 to about 100,000 Daltons. When a polysaccharide is linked to the cellulose, it can have a molecular weight exclusion limit of greater than about 30,000 Daltons.

Articles which contain cellulose can be barriers, structures, or devices useful in surgery, diagnostic procedures, or wound treatment. For example, an article containing cellulose can be a bandage, suture, dressing, gauze, gel, foam, web, film, tape, or patch. An article containing cellulose can include a cotton material, e.g., cotton gauze. The article can also optionally include adhesives or polymeric laminating materials.

Hemostatic compositions of the present invention are useful for accelerating blood clotting at an active bleeding wound site. Prior to the application of a hemostatic composition, an active bleeding wound site may be characterized in that it bleeds at a rate of from about 0.5 ml/min to about 1000 ml/min. After application of a hemostatic composition, the active bleeding wound site may bleed at a rate of less than 0.03 ml/min. For example, the rate of less than 0.03 ml/min. may be achieved in from about 2 to about 20 minutes, and in certain embodiments in less than about 5 minutes.

A hemostatic composition can comprise a second polysaccharide covalently linked to the cellulose and, optionally, to the first polysaccharide. The second polysaccharide may have a different molecular weight than the first polysaccharide. For example, the second polysaccharide may be dextran having a molecular weight from about 800,000 to about 2M. Alternatively, the second polysaccharide may be physically trapped by the covalent linking of the first polysaccharide to the cellulose.

In other embodiments, hemostatic compositions of the present invention can include an article comprising cellulose in association with a polysaccharide ionically linked to itself (cross-linked). For example, the article comprising cellulose may be coated with, immersed in, or soaked in the polysaccharide, which is subsequently ionically cross-linked. The polysaccharide may be further covalently linked to the cellulose of the article. In addition, in certain embodiments, the polysaccharide may be physically trapped in fibers of the article comprising cellulose.

One example of a polysaccharide that can be ionically cross-linked is alginate. Alginate can be ionically cross-linked to itself with metal cations, including $Mg^{2+}$; $Ni^{2+}$; $Ca^{2+}$; $Sr^{2+}$; $Ba^{2+}$; $Zn^{2+}$; $Cd^{2+}$; $Cu^{2+}$; $Pb^{2+}$; $Fe^{3+}$; and $Al^{3+}$. In some embodiments, the cation is $Ca^{2+}$. A second polysaccharide, such as dextran, can also be physically trapped, e.g., by the network formed by the ionic cross-linking of the first polysaccharide. Dextran can be in the form of cross-linked beads, e.g., dextran that has been previously cross-linked to itself. Dextran can be covalently linked to the bandage, e.g. by linking dextran to the cellulose with epichlorohydrin.

In another aspect, a hemostatic composition can include dextran-alginate spheres, such as ionically linked dextran-alginate spheres, or covalently linked dextran-alginate spheres, or both ionically and covalently linked dextran-alginate spheres.

In another aspect of the invention, hemostatic compositions are provided that include additional agents, such as analgesics, steroids, antihistamines, anesthetics, bactericides, disinfectants, fungicides, vasoconstrictors, hemostatics, chemotherapeutic drugs, antibiotics, keratolytics, cauterizing agents, antiviral drugs, epidermal growth factor, fibroblast growth factors, transforming growth factors, glycoproteins, collagen, fibrinogen, fibrin, humectants, preservatives, lymphokines, cytokines, odor controlling materials, vitamins, and clotting factors.

The invention also provides methods for making hemostatic compositions. Hemostatic compositions of the present invention can be made by incubating a linking agent with a polysaccharide and an article comprising cellulose to form a hemostatic composition having the polysaccharide covalently linked to the cellulose.

The linking agent may be any linking agent useful for linking available hydroxyl groups on cellulose with available hydroxyl groups on a polysaccharide. Examples include epichlorohydrin, dichlorohydrin, diepoxyburan, disepoxypropyl ether, or ethylene-glyco-bis-epoxypropylether. The incubation step may occur in an aqueous alkaline solution. The temperature of the incubation step can range from about 40° C. to about 70° C. In certain embodiments, the temperature is about 50° C. The incubation step can occur for about 1 to about 24 hours. In additions the incubation step can be in the presence of a stabilizing solution, e.g., a solution designed to prevent or limit evaporation of water. The stabilizing solution can include cellulose acetate butyrate. The covalently linked polysaccharide may have a molecular weight exclusion limit of greater than 30,000 Daltons.

In certain embodiments of the method, the polysaccharide is dextran. The dextran can be in the form of covalently cross-linked beads. The molecular weight of the dextran can range from about 10,000 to about 2M, or from about 20,000 to about 100,000 Daltons. The incubation step may be occur in an aqueous alkaline solution having about 12% to about 75% dextran.

In another aspect, the invention provides a method of making a composition including incubating a polysaccharide and a cation with an article containing cellulose in order to form a hemostatic composition having the article containing cellulose in association with an ionically cross-linked polysaccharide. The polysaccharide may be further covalently linked to the cellulose. The cation may be, for example, $Ca^{2+}$. The $Ca^{2+}$ may be in the form of, or derived from, $Ca^{2+}$-loaded cross-linked dextran beads. The polysaccharide may be sodium alginate or a derivative of alginic acid, including salts of alginic acid.

In certain embodiments, the incubation step includes a second polysaccharide; the second polysaccharide may become physically trapped in the three dimensional network formed by the ionic cross-linking of the first polysaccharide. The second polysaccharide may be dextran, e.g., dextran in the form of cross-linked beads. The second polysaccharide may be further covalently linked to the cellulose, e.g., through a linking agent such as epichlorohydrin.

In another aspect, the invention provides a method for manufacturing a composition, where the method includes the step of mixing an aqueous phase alkaline polysaccharide solution with an organic phase stabilizing agent solution to form a mixture having polysaccharide spheres; incubating a cross-linking agent with the mixture to cross-link the polysaccharide spheres; isolating the cross-linked polysaccharide spheres; and coating an article comprising a sodium alginate solution with the cross-linked polysaccharide spheres. The method can include removing the organic phase stabilizing agent from the mixture, e.g., prior to isolating the cross-linked polysaccharide spheres. The method can also include exposing the cross-linked polysaccharide spheres to a solution comprising $Ca^{2+}$ ions, e.g., washing the cross-linked polysaccharide spheres in a $Ca^{2+}$ solution. The polysaccharide may be dextran, and the organic phase stabilizing agent solution may include cellulose acetate butyrate.

In certain embodiments of the method, cross-linked polysaccharide spheres are between about 30 to about 500 μm in size. The mixing and incubating steps may occur at a temperature of from about 40° C. to about 70° C. The coating step can include spraying the article with the cross-linked polysaccharide spheres. The invention also relates to hemostatic compositions manufactured according to the above method.

In a further aspect, another method for manufacturing a composition is provided. The method includes the steps of providing an aqueous phase alkaline solution having dextran and sodium alginate therein; preparing dextran-alginate spheres from the aqueous phase alkaline solution; and incubating the dextran-alginate spheres with a linking agent to link said dextran-alginate spheres. Dextran-alginate spheres can be prepared by any method conventional in the art, including the use of a mechanical droplet generator. A linking agent may covalently or ionically link or cross-link the dextran-alginate spheres. Accordingly, a linking agent may be epichlorohydrin or a $Ca^{2+}$-containing salt such as calcium chloride. The dextran-alginate spheres may be linked with a $Ca^{2+}$ linking agent, and then linked with an epichlorohydrin linking agent, or the linking can be performed in the reverse order, or simultaneously. The method can further including coating, e.g., spraying, an article, such as an article comprising sodium alginate, with the linked dextran-alginate spheres. The invention also includes hemostatic compositions manufactured according to the method.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patents, patent applications, and other references mentioned herein are incorporated by reference in their entirety. In case of conflict, the present specification, including definitions, will control. In addition, the materials, methods, and examples are illustrative only and not meant to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

As used herein, the terms "linking" or "linked" are meant to indicate either a covalent or ionic link, either direct or mediated by a chemical moiety or an ion, between two chemically distinct entities, e.g., dextran linked to cellulose. The term "cross-link" is meant to indicate a covalent or ionic link, either direct or mediated by a chemical moiety or ion, between two chemically similar moieties, e.g., dextran cross-linked to itself; alginate cross-linked to itself. The chemically similar moieties do not have to be identical. For example, dextran having a particular average molecular weight range includes dextran molecules of a variety of molecular weights, and thus the dextran molecules are not identical but chemically similar. When dextran molecules having an average molecular weight range are linked, e.g., covalently linked with epichlorohydrin, they are said to be "cross-linked."

The terms "spheres," "particles," or "beads," when used in the context of the present invention, are not meant to imply different sizes, but are meant to be interchangeable terms describing an embodiment of a composition.

The term "active bleeding wound site" means, at a minimum, that unclotted blood is present in the wound, e.g., extravascular blood, particularly where the surface of a tissue has been broken or an artery, vein, or capillary system has been compromised. The rate of blood flow from an active bleeding wound site can vary, depending upon the nature of the wound. In some cases, an active bleeding wound site will exhibit blood flow at a rate from about at a rate of from about 0.5 ml/min to about 1000 ml/min. Some active bleeding wound sites may exhibit higher rates of blood flow, e.g., punctures of major arteries such as the aorta. After application of the hemostatic composition, the active bleeding wound site may bleed at a rate of less than 0.03 ml/min. For example, the rate of less than 0.03 ml/min. may be achieved in from about 2 to about 20 minutes, and in certain embodiments in less than about 5 minutes.

Hemostatic Compositions

The invention relates to hemostatic compositions used to promote hemostasis at active bleeding wound sites. While not being bound by any theory, it is believed that the hemostatic compositions of the present invention control bleeding by initiating and accelerating blood clotting. The hemostatic compositions of the present invention activate platelets and concentrate high molecular weight components of the coagulation cascade (e.g., clotting factors) by excluding high molecular weight components of the cascade, while absorbing the lower molecular weight components in blood. Accordingly, coagulation cascade components having a molecular weight higher than about 30,000 Daltons are excluded, including fibrinogen (MW 340,000); prothrombin (MW 70,000); thrombin (MW 34,000); Factor V (MW 330,000); Factor VII (MW 50,000); Factor VIII (MW 320,000); von Willebrand factor (MW >850,000); Factor IX (MW 57,000); Factor X (MW 59,000); Factor XI (MW 143,000); Factor XII (MW 76,000); Factor XIII (MW 320,000); high MW kininogen (Fitzgerald Factor) (MW 120,000–200,000), and prekallikrein (Fletcher Factor) (MW 85,000–100,000). In addition, laboratory experiments indicate that platelets aggregate around the hemostatic compositions of the present invention when exposed to blood. The net result is that concentrated clotting factors (coagulation cascade components) and activated platelets activate the conversion of prothrombin to thrombin in the presence of $Ca^{2+}$, which subsequently catalyzes the conversion of fibrinogen to insoluble fibrin multimers, e.g, a fibrin clot. Additional information on the clotting cascade and hemostatic compositions containing fibrin can be found in U.S. Pat. No. 5,773,033.

Hemostatic compositions typically include an article comprising cellulose, e.g., cotton gauze, and a polysaccharide covalently linked to the cellulose. In other embodiments, hemostatic compositions include an article comprising cellulose in association with a polysaccharide that is ionically cross-linked. The polysaccharide can be further covalently linked to the cellulose. Hemostatic compositions can include additional polysaccharides covalently linked to either or both of the cellulose and the first polysaccharide.

Other embodiments of hemostatic compositions include linked and cross-linked polysaccharide spheres, optionally loaded with a cation, e.g., $Ca^{2+}$.

It should be noted that certain hemostatic compositions comprise both a macroscopic structure (e.g., an article) and a microscopic structure (e.g., networks of polysaccharide cross-linkages or networks of polysaccharide covalent linkages to cellulose). Some hemostatic compositions therefore form three dimensional networks of a polysaccharide, either as ionically linked chains or covalently bound to the cellulose of the article. Accordingly, in some embodiments, a second polysaccharide may be physically trapped by the network formed by the first polysaccharide.

Accordingly, in one aspect, a hemostatic composition includes an article containing cellulose and a polysaccharide, such as dextran, starch, or alginate, covalently linked to the cellulose. The article may include natural or synthetic celluloses (e.g., cellulose acetate, cellulose butyrate, cellulose propionate). The polysaccharide chosen should be safe for in vivo use, e.g., non-allergenic, non-toxic, and preferably non-metabolized. Polysaccharides for clinical use are known in the art and available from a variety of sources. See, e.g., U.S. Pat. No. 6,303,585.

As used herein, covalent linkages encompass bonds from any of the available chemical moieties of the polysaccharide to any of the available chemical moieties of the cellulose. For example, if the polysaccharide dextran is used, hydroxyl moieties on dextran can be covalently linked to hydroxyl moieties on cellulose through the linking agent epichlorohydrin. In that case, a glyceryl bridge linking dextran to cellulose is formed. For additional information, see Flodin, P., and Ingelman, B., "Process for the Manufacture of Hydrophilic High Molecular Weight Substances," British Patent No. 854, 715; and Flodin, P. "Chapter 2: The Preparation of Dextran Gels," *Dextran Gels and Their Applications in Gel Filtration*, Pharmacia, Uppsala Sweden, 1962, pages 14–26.

The average molecular weight range of the polysaccharide can vary, but typically ranges from about 10,000 to about 2M Daltons. The molecular weight range chosen will affect the molecular weight exclusion limit of the covalently linked polysaccharide, and thus its ability to exclude the coagulation components and concentrate them.

Dextran is a high molecular weight polysaccharide that is water-soluble. It is not metabolized by humans, and is non-toxic and tolerated well by most animals, including humans. The average molecular weight of dextran used in the present invention can range from about 10,000 to about 2,000,000 Daltons, or from about 20,000 to about 100,000 Daltons.

Dextran can be in the form of beads, e.g., covalently cross-linked beads, before it is linked covalently to the cellulose. Dextran beads can exhibit a range of sizes, e.g., from about 30 to about 500 µm. Dextran beads are commercially available, e.g., as Sephadex™ (Pharmacia); see, for example UK 974,054. Alternatively, dextran beads or particles may be formed during the preparation of the hemostatic composition, e.g., from the covalent cross-linking of previously uncross-linked dextran molecules.

In other embodiments, dextran may be in solution form, e.g., uncross-linked, before it is covalently linked to the cellulose. Dextran may be covalently linked to the cellulose and covalently cross-linked to itself, e.g., when exposed to a linking agent such as epichlorohydrin. When dextran is in solution form (e.g., uncross-linked), the dextran molecules may coat all or a component of the article, such as fibers of a cotton bandage, so that it subsequently forms a three-dimensional microscopic linked network or mesh when it is covalently linked to the cellulose and covalently cross-linked to itself. Dextran beads linked to cellulose or a cellulose-dextran mesh as described previously contribute to the ability of a hemostatic composition to exclude high molecular weight components of the coagulation cascade.

The average molecular weight of the polysaccharide, the degree of linking of the polysaccharide to cellulose, and any cross-linking of the polysaccharide (e.g., to itself) are factors in the molecular weight exclusion limit of the polysaccharide in a hemostatic compositon and the water regain of a hemostatic composition. Water regain is defined as the weight of water taken up by 1 g of dry hemostatic composition and can be determined by methods known in the art. For example, it is known that small changes in dextran concentration or linking agent concentration (e.g., epichlorohydrin) can result in dramatic changes in water regain. Typically, at lower molecular weights of dextran, a higher water regain results. See Flodin, P., "Chapter 2: The Preparation of Dextran Gels," *Dextran Gels and Their Applications in Gel Filtration*, Pharmacia, Uppsala Sweden, 1962, pages 14–26.

Similarly, the degree of hydration of the polysaccharide also affects the molecular weight exclusion limit. As the degree of hydration increases, the molecular weight exclusion limit of the polysaccharide usually increases. Typically, when dextran is linked to cellulose, the dextran will have a molecular weight exclusion limit of greater than about 30,000 Daltons, thus effectively excluding the components of the coagulation cascade and concentrating them on the microscopic surface of the hemostatic composition.

Articles which contain cellulose can be any barriers, structures, or devices useful in surgery, diagnostic procedures, or wound treatment. For example, an article containing cellulose can be a bandage, suture, dressing, gauze, gel, foam, web, film, tape, or patch. An article containing cellulose can include a cotton material, e.g., cotton gauze. The article should allow the polysaccharide linked to the cellulose to interact with the wound site.

A hemostatic composition can comprise a second polysaccharide covalently linked to cellulose. The second polysaccharide may have a different molecular weight than the first polysaccharide. For example, the second polysaccharide may be dextran having a molecular weight from about 800,000 to about 2M. The second polysaccharide may be covalently linked to the cellulose at a time after the first polysaccharide, at the same time as the first polysaccharide, or at a time before the first polysaccharide.

In other embodiments, hemostatic compositions of the present invention can include an article containing cellulose in association with an ionically cross-linked polysaccharide. The polysaccharide may be further covalently linked to the cellulose. In this context, ionic linkages include ion-mediated bonds between available chemical moieties on the polysaccharide. Typical chemical moieties that can be mediated with an ion (e.g., a cation) include hydroxyl moieties. For example, sodium alginate or alginic acid salts can be ionically linked with metal cations, including $Mg^{2+}$, $Ni^{2+}$, $Ca^{2+}$, $Sr^{2+}$, $Ba^{2+}$, $Zn^{2+}$, $Cd^{2+}$, $Cu^{2+}$, $Pb^{2+}$, $Fe^{3+}$, and $Al^{3+}$. Typically, $Ca^{2+}$ may be used. The alginate can be of any type, including type G (L-guluronic acid) or type M (D-mannuronic acid), or mixed M and G. For more information on alginate, see U.S. Pat. No. 5,144,016.

In certain embodiments, a second polysaccharide, such as dextran, can be physically trapped in the network formed by the ionic cross-linking of the first polysaccharide. Dextran can be in the form of covalently cross-linked beads, e.g., dextran that has been previously cross-linked to itself with epichlorohydrin, or Sephadex™ beads. Alternatively, the dextran can be in solution form (e.g., uncross-linked), as described above. In addition, dextran can be covalently linked to the cellulose, e.g. by linking dextran to the cellulose with epichlorohydrin. Accordingly, dextran may become cross-linked to itself.

Other embodiments of hemostatic compositions include dextran-alginate spheres, such as ionically linked dextran-alginate spheres, or covalently linked dextran-alginate spheres, or both ionically and covalently linked dextran-alginate spheres. In addition, cross-linked dextran spheres loaded with $Ca^{2+}$ ions are also included as hemostatic compositions of the present invention.

Hemostatic compositions can include additional agents, such as analgesics, steroids, antihistamines, anesthetics, bactericides, disinfectants, fungicides, vasoconstrictors, hemostatics, chemotherapeutic drugs, antibiotics, keratolytics, cauterizing agents, antiviral drugs, epidermal growth factor, fibroblast growth factors, transforming growth factors, glycoproteins, collagen, fibrinogen, fibrin, humectants, preservatives, lymphokines, cytokines, odor controlling materials, vitamins, and clotting factors. For further information on these additional agents for incorporation, refer to WO 00/27327.

Hemostatic compositions may be used in combination with polymeric laminating materials and adhesives to provide both mechanical support and flexibility to an article and to facilitate adhesion to the wound. Additional information on such polymeric laminating materials and adhesives for use in the present invention can be found in, e.g., WO 00/27327.

Pharmaceutical Compositions

The present invention also contemplates pharmaceutical compositions comprising certain hemostatic compositions of the present invention, e.g., dextran-alginate linked spheres or calcium-loaded cross-linked dextran spheres. Pharmaceutical compositions may be formulated in conventional manners using one or more physiologically acceptable carriers containing excipients and auxiliaries. Proper formulation is dependent upon the route of administration chosen.

A "pharmaceutically acceptable carrier" (also referred to herein as an "excipient") is a pharmaceutically acceptable solvent, suspending agent, or any other pharmacologically inert vehicle for delivering one or more hemostatic compositions to a subject. Pharmaceutically acceptable carriers can be liquid or solid, and can be selected with the planned manner of administration in mind so as to provide for the desired bulk, consistency, and other pertinent transport and chemical properties, when combined with a hemostatic composition. Other components may be present in a pharmaceutical composition, if desired.

Pharmaceutical compositions of the present invention can be administered by a number of methods depending upon the area to be treated. Administration can be, for example, topical or parenteral. Administration can be rapid (e.g., by injection) or can occur over a period of time. For treating tissues in the central nervous system, pharmaceutical compositions can be administered by injection or infusion into the cerebrospinal fluid, preferably with one or more agents capable of promoting penetration of the pharmaceutical composition across the blood-brain barrier.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include patches, ointments, lotions, creams, gels, drops, suppositories, sprays, liquids, and powders. Conventional pharmaceutical carriers, aqueous, powder or oily bases, thickeners and the like may be necessary or desirable.

Compositions and formulations for parenteral administration can include sterile aqueous solutions, which also can contain buffers, diluents and other suitable additives (e.g., penetration enhancers, carrier compounds and other pharmaceutically acceptable carriers).

Pharmaceutical compositions of the present invention include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Pharmaceutical compositions of the invention further encompass any pharmaceutically acceptable salts, esters, or salts of such esters, or any other compound which, upon administration to an animal including a human, is capable of providing (directly or indirectly) the biologically active metabolite or residue thereof. The term "pharmaceutically acceptable salts" refers to physiologically and pharmaceutically acceptable salts of the hemostatic compositions of the invention (i.e., salts that retain the desired biological activity without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed from elemental anions (e.g., chlorine, bromine, and iodine).

Methods of Controlling Bleeding

In one aspect of the invention, a method for controlling bleeding at an active bleeding wound site of an animal is provided. The method includes applying a hemostatic composition to the active bleeding wound site. Application of the hemostatic composition typically includes contacting the hemostatic composition with the wound or bleeding site surface. The hemostatic composition is maintained in contact with the wound or bleeding site for a period of time sufficient to control the bleeding, e.g., to clot the blood, slow the rate of bleeding, or stop the bleeding. The application may include the use of pressure, e.g., by using an elastic bandage to maintain contact with the bleeding site. Alternatively, an internal wound may be packed with a hemostatic composition until hemostasis is achieved. In other embodiments, a hemostatic composition is delivered to the wound site. For example, a catheter or needle may be used to deliver a hemostatic composition to an intravascular puncture site or to a biopsy site. The catheter or the needle may be optionally coated with a hemostatic composition of the present invention.

Usually a hemostatic composition can control bleeding, for example, to a rate of less than 0.03 ml/min, in a period of from about 2 to about 20 minutes. In certain embodiments, bleeding stops immediately, or in less than about 5 minutes.

Typically a hemostatic compositions of the present invention will be used to inhibit or completely stop bleeding of a parenchymal organ, such as the liver, kidney, spleen, pancreas, or lungs; or to control bleeding during surgery (e.g., abdominal, vascular, gynecological, dental, tissue transplantation surgery, etc.). For example, percutaneous needle biopsies are common interventional medical procedures. Possible complications of needle biopsies, however, include bleeding at the biopsy site. The amount of bleeding is related to the needle size, tissue sample size, location of the biopsy, and vascularization of the tissue. Hemostatic compositions of the present invention can be used to promote hemostasis at needle biopsy sites. Biopsy needles may either be coated with hemostatic compositions of the present invention, or may be used to deliver a hemostatic composition to the biopsy site. For more information on biopsy tracts, see U.S. Pat. No. 6,447,534.

Similarly, catheterization and interventional procedures, such as angioplasty and stenting, generally are performed by inserting a hollow needle through a patient's skin and muscle tissue into the vascular system. A guide wire is then typically passed through the needle lumen into a blood vessel. The needle is removed and an introducer sheath is advanced over the guide wire into the vessel, and a catheter is typically passed through the lumen of the introducer sheath and advanced over the guide wire for positioning. Upon completion of the medical procedure, the catheter and introducer sheath are removed, often leaving a puncture site in the vessel, with associated bleeding. Hemostatic compositions of the present invention may be used to coat the exterior of catheters, stents, introducer sheath, and guide wires, etc., or may be delivered, e.g., via a catheter, to the puncture site in order to promote hemostasis. For additional information, see U.S. Pat. No. 6,391,048.

The amount of hemostatic composition to be used will vary with the patient, the wound, and the composition employed. For example, hemostatic compositions with varying water regains can be assembled (e.g., stacked in descending order) for use in major bleeding to attain hemostasis.

Methods for Making Hemostatic Compositions

In another aspect, the invention provides methods for making hemostatic compositions. The hemostatic compositions of the present invention can be made by incubating a linking agent with a polysaccharide and an article containing cellulose to form a hemostatic composition having the polysaccharide covalently linked to the cellulose.

Any biologically compatible bifunctional or heterobifunctional reagent may be used as the linking agent, including reagents with halogens, epoxides, hydroxy succinimide esters, aldehydes, activated thiols, or other moieties for reacting free amines, hydroxides, hydroxyls, or sulfhydryls on the bandage or on the polysaccharide. The bandage may be modified, e.g., derivatized, to incorporate reactive moieties such as amines or sulfhydryls for reacting with a particular linking agent. The polysaccharide may also be modified, e.g., derivatized, in a similar manner, provided that the polysaccharide so derivatized remains pharmaceutically suitable for animal, e.g., human use. The linking agent may be epichlorohydrin, dichlorohydrin, diepoxybutane, disepoxypropyl ether, or ethylene-glyco-bis-epoxypropylether. For additional information, see Flodin, P., and Ingelman, B., "Process for the Manufacture of Hydrophilic High Molecular Weight Substances," British Patent No. 854, 715; and Flodin, P., "Chapter 2: The Preparation of Dextran Gels," *Dextran Gels and Their Applications in Gel Filtration*, Pharmacia, Uppsala Sweden, 1962, pages 14–26.

The incubation step may occur in an aqueous alkaline solution. Typically, the polysaccharide is from about 10% to about 80% wt/vol of the aqueous alkaline solution. The concentration of the linking agent in the incubation step can range from about 2% to about 20% wt/wt of the polysaccharide.

The temperature of the incubation step can range from about 40° C. to about 70° C. In certain embodiments, the temperature is about 50° C. The incubation step can occur for about 1 to about 24 hours. The incubating step may also include agitation of the reagents. In addition, the incubation step can be in the presence of a stabilizing solution, e.g., a solution designed to prevent or limit evaporation of water. The stabilizing solution can include cellulose acetate butyrate. The method can also include neutralizing the aqueous alkaline solution, e.g., with an acid such as HCl at a concentration of from 1 to 5M.

The hemostatic composition can be washed with an aqueous solution, e.g., distilled water, or an aqueous alcoholic wash, e.g., 50/50 vol/vol EtOH/water. The hemostatic composition can be serially washed in increasing amounts of an alcoholic wash, such as 25%, 50%, 75%, and 100% EtOH. The alcohol wash solution can contain a humectant, e.g., glycerin, at a concentration of about 0.1 to about 2.0%. The hemostatic composition can be dried, e.g., at about 50° C. to about 80° C. For example, the hemostatic composition can be dried at 70° C. After drying, the covalently linked polysaccharide may have a molecular weight exclusion limit of greater than 30,000 Daltons.

In certain embodiments of the method, the polysaccharide is dextran. The dextran can be in the form of covalently cross-linked beads. The molecular weight of the dextran can range from about 10,000 to about 2M, or from about 20,000 to about 100,000 Daltons. Typically, dextran of MW 40,000 is used. The incubation step may be occur in an aqueous alkaline solution having about 12 to about 75% dextran wt/vol.

In another aspect, the invention provides a method of making a hemostatic composition including incubating a polysaccharide and a cation with an article containing cellulose in order to form a hemostatic composition having the article containing cellulose in association with an ionically cross-linked polysaccharide. The polysaccharide may be further covalently linked to the cellulose. The cation may be as described previously, including, for example, Ca2+. The Ca2+ may be in the form of, or derived from, Ca2+-loaded cross-linked, dextran beads. The polysaccharide may be sodium alginate or derivatives of alginic acid, including salts of alginic acid. Aqueous and alcoholic washes of the hemostatic composition can be performed, as described previously.

In certain embodiments, the incubation step includes a second polysaccharide. The second polysaccharide may be dextran, e.g., dextran in the form of covalently cross-linked beads. The second polysaccharide may be physically trapped, e.g., in the three-dimensional network formed by the ionic cross-linking of the first polysaccharide. The second polysaccharide may be further covalently linked to the bandage, e.g., through a linking agent such as epichlorohydrin.

In one embodiment, an article such as cellulose gauze is immersed in a solution of a first polysaccharide (e.g., about 1 to 5% sodium alginate) and a second polysaccharide (e.g., 20% dextran, avg. molecular weight 40,000). The first polysaccharide is ionically cross-linked with a cation solution, e.g., Ca2+ from a solution having about 0.5 to about 10% aqueous calcium chloride. The Ca2+ concentration can be reduced with serial washes, e.g., to reduce the Ca2+ concentration to about 0.5% Ca2+. The first or second polysaccharide, or both, may then be covalently linked to the cellulose and/or cross-linked using an aqueous alkaline solution (e.g., 20% NaOH) of a linking agent, e.g., epichlorohydrin (e.g., at about 3–6% of the weight of the second polysaccharide). The resulting hemostatic composition may be dried as described previously.

In another embodiment of the present invention, cross-linked polysaccharide spheres can be mixed with a Ca2+-alcoholic wash solution (e.g., 1% calcium chloride in neat alcohol). The cross-linked polysaccharide spheres can be purchased, e.g., as Sephadex™, or can be prepared from an aqueous alkaline polysaccharide solution and a cross-linking agent (e.g., dextran cross-linked with epichlorohydrin), as discussed previously. After washing in the Ca2+-alcohol solution, the cross-linked polysaccharide spheres have Ca2+ in their pores, e.g., are Ca2+-loaded spheres, and can be used to coat an article, e.g., sprayed onto a bandage, that has been previously soaked or immersed in a polysaccharide solution, e.g., sodium alginate, at a concentration of about 0.5–5% polysaccharide. In certain embodiments, Ca2+ from the cross-linked spheres exchanges with the sodium from the sodium alginate solution, resulting in ionically cross-linked calcium alginate, which physically traps cross-linked polysaccharide spheres in the three-dimensional network of ionic bonding. The hemostatic composition so formed may be dried as discussed previously.

In another aspect, the invention provides a method for manufacturing a composition, where the method includes the step of mixing an aqueous phase alkaline polysaccharide solution with an organic phase stabilizing agent solution to form a mixture having polysaccharide spheres; incubating a cross-linking agent with the mixture to cross-link the polysaccharide spheres; isolating the cross-linked polysaccharide spheres; and coating an article comprising a sodium alginate solution with the cross-linked polysaccharide spheres. The method can include removing the organic phase stabilizing agent from the mixture, e.g., prior to isolating the cross-linked polysaccharide spheres. The method can also include exposing the cross-linked polysaccharide spheres to a solution comprising Ca2+ ions, e.g., washing the cross-linked polysaccharide spheres in a Ca2+ solution. The polysaccharide may be dextran, and the organic phase stabilizing agent solution may include cellulose acetate butyrate.

In certain embodiments of the method, the cross-linked polysaccharide spheres are between about 30 to about 500 µm in size. The mixing and incubating steps may occur at a temperature of from about 40° C. to about 70° C. The coating step can include spraying the article with the cross-linked polysaccharide spheres. The invention also relates to hemostatic compositions manufactured according to the above method.

In a further aspect, another method for manufacturing a composition is provided. The method includes the steps of providing an aqueous phase alkaline solution having dextran and sodium alginate therein; preparing dextran-alginate spheres from the aqueous phase alkaline solution; and incubating the dextran-alginate spheres with a linking agent to form linked dextran-alginate spheres. The dextran-alginate spheres can be prepared by any method conventional in the art, including the use of a mechanical droplet generator or an air knife.

The linking agent may covalently or ionically link and/or cross-link the dextran-alginate spheres. Accordingly, the linking agent may be epichlorohydrin or a cation as described previously, e.g., a Ca2+-containing salt. The dextran-alginate spheres may be first linked with a cation linking agent, and then linked with an epichlorohydrin linking agent, or vice versa. The dextran-alginate spheres may be linked simultaneously with a cation linking agent and an epichlorohydrin linking agent. The method can further including coating, e.g., spraying, an article with the linked dextran-alginate spheres. The invention also is directed to hemostatic compositions manufactured according to the method.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Cotton-Dextran Compositions

Pharmaceutically acceptable cotton-based compositions were incubated with dextran (40,000 MW) in an alkaline epichlorohydrin solution (20% dextran in NaOH wt/vol; epichlorohydrin at about 3 to 6% wt/wt dextran). The solutions were allowed to react for about 1 to about 16 hours at a temperature range from about ambient room temperature to about 60° C. The resulting cross-linking reactions were subsequently neutralized using a 1 to 5 Molar HCl solution.

The cross-linked and linked dextran-cotton hemostatic compositions were washed about 4 times with distilled water. The products were further washed twice with a 50% distilled water/alcohol solution, then with a 75% alcohol solution, and lastly with a 100% alcohol solution, to remove excess epichlorohydrin. A final alcohol wash solution contained about 0.1 to about 2% glycerin to keep the composition from becoming brittle. The hemostatic composition was dried at about 70° C. overnight.

Example 2

Cotton-Alginate-Dextran Compositions

A stabilizing agent, such as cellulose acetate butyrate was dissolved in ethylene dichloride at 3% wt/vol and heated to about 50° C. while stirring at about 200 RPM in a 1–2 liter cylindrical reaction vessel. Dextran (MW 40,000) was dissolved in water at 15% wt/vol with 5N NaOH at 2% of the dextran weight. The dextran solution was gradually added to the stabilizing mixture with continued heating and stirring. When droplets of the desired size were formed (30–500 µm), a cross-linking agent such as epichlorohydrin was added to the vessel at 20% of the dextran weight. The reaction formed cross-linked gel spheres in 1–3 hours, but was allowed to proceed up to 16 hours before termination. Acetone was added and decanted twice to remove the stabilizer (cellulose acetate butyrate). The spheres were then treated with NaOH (equal parts of 2N NaOH and 95% ethyl alcohol) for about 15 mins., and neutralized with dilute acid (1N HCl) before filtration and washing with water. The swollen spheres were shrunk with alcohol treatment (25, 50, 75, 100% serial alcohol washes).

Dry calcium chloride was mixed with a second 100% alcohol wash solution (1% calcium chloride in alcohol), which was used to wash the cross-linked dextran particles. The alcohol was evaporated off, trapping the calcium in the pores of the dextran particles. The final products were dry cross-linked dextran-calcium ion compositions.

Pharmaceutically acceptable cotton-based compositions were immersed (dipped) into a sodium alginate liquid solution (0.5–4%). After removal from the solution, the wet sodium alginate coated cotton materials were sprayed or dusted with the cross-linked dextran calcium compositions. Calcium exchanged with sodium, resulting in cross-linked calcium alginate. The cotton-dextran-alginate hemostatic compositions were then dried at 70° C. overnight.

Example 3

Alternative Method to Prepare Cotton-Dextran-Alginate Compositions

Cotton gauzes were immersed in solutions of 1 to 5% sodium alginate and 20% dextran (40,000 MW). The mixtures were cross-linked and linked with about 0.5% to about 10% aqueous calcium chloride solution. The compositions were washed to reduce Ca2+ concentration to about 0.5% Ca2+.

Dextran-alginate cross-linking solutions were prepared using an aqueous alkaline epichlorohydrin solution, where the concentration of the epichlorohydrin was from about 3 to about 6% by weight of the dextran. The solutions included about 20% NaOH. The resulting hemostatic compositions were allowed to dry at ambient to about 60° C. overnight.

Example 4

Cotton-Dextran Compositions

Dextran (MW 40,000) was dissolved in 1N NaOH at a range of 18–69% wt/vol of dextran in the alkaline solution. Epichlorohydrin was added to a concentration of 20% of the dextran by weight at room temperature. Pharmaceutically acceptable cotton (cellulose) gauzes were added to the alkaline epichlorohydrin solutions. The solutions were allowed to react with agitation at 25° C. to 70° C. The mixtures were heated until a cross-linked dextran-cellulose gel formed on the gauze fibers, from 1–6 hours, up to 24 hours. After neutralization with dilute HCl (1N), successive washes removed excess reaction products and impurities: four times in distilled water, then with increasing concentrations of alcohol (25, 50, 75, 100%). A final alcohol wash of 100% EtOH contained from 0.1 to 2.0% glycerin to keep the compositions pliable. The resulting hemostatic compositions were dried at about 70° C. overnight.

The water regain for the hemostatic compositions ranged from 2.5 ml/g to 35 ml/g. For information on water regain, see Flodin, P., *Dextran Gels and Their Applications in Gel Filtration*, Pharmacia, Uppsala Sweden, 1962, pages 31–32.

Example 5

Cellulose-Dextran Composition 150 g of dextran (MW 40,000) was dissolved in 300 ml 1N NaOH. 30 g epichlorohydrin was quickly mixed with the dextran solution at room temperature. A pharmaceutically acceptable cellulose gauze was dipped in the alkaline epichlorohydrin solution to thoroughly coat the fibers with the reaction solution, then placed in a flat-bottomed dish. The gauze was heated to 50° C. in a humidified atmosphere, with gentle rocking after 1 hour, until a dextran-cellulose gel formed on the gauze fibers, typically in 1–2 hours. Heating was continued until the desired end-point, up to 24 hours. The gauze was neutralized, washed, treated with glycerin, and dried as described previously. The water regain was 7.5 ml/g.

Example 6

Cellulose-Dextran Composition

Dextran (MW 40,000) was dissolved in 1N NaOH (34% dextran wt/vol of the alkaline solution). Epichlorohydrin was added to a concentration of 20% of the dextran by weight at room temperature. A pharmaceutically acceptable cellulose fiber based composition, 16-ply 4×4 gauze, was dipped in the alkaline epichlorohydrin solution to thoroughly coat the fibers with the reaction solution, then placed in a flat bottomed dish. To prevent concentrating the reaction solution by evaporation, a stabilizing solution of cellulose acetate butyrate in ethylene dichloride (3% wt/vol), which is immiscible in water, was used to cover the gauze. The gauze was heated at 50° C., with gentle rocking after 1 hr., until a cross-linked and linked dextran-cellulose gel formed on the gauze fibers, typically in about 2 to 3 hours. Heating was continued until the desired endpoint, up to 24 hours. Acetone was added and decanted twice to remove the stabilizer. The gauze was neutralized with dilute HCl and washed as described previously in aqueous alcohol and alcohol solutions and dried at about 70° C. overnight. The water regain was 15 ml/g.

Example 7

Cellulose Dextran Composition

Dextran (MW 40,000) was dissolved in 1N NaOH and reacted with gauze in the presence of epichlorohydrin, followed by neutralization, washing, and drying as described above. Cellulose-dextran compositions were made by varying the volume of dextran in the solvent from 12 to 75 wt/vol to produce hemostatic composition with water regains ranging from 5 ml/g to 35 ml/g. The compositions can be assembled for use in major bleeding by stacking them in descending order (e.g., 35 ml/g to 5 ml/g) to attain hemostasis.

Example 8

Dextran-Calcium Spheres

A non-ionic polymer substance was dissolved in a suitable solvent with an alkaline solution added as a cross-linking catalyst. A stabilizer was dissolved in a solvent that was immiscible with the polymer solvent and placed in a cylindrical vessel. The stabilizer solution formed the continuous phase and was heated with regular stirring. When the polymer solution was added to the stabilizer solution, a biphasic system formed in which the polymer droplets became the dispersed phase. A bifunctional cross-linking agent was added to the system which caused co-polymerization (cross-linking) of the polymer to form gel spheres. After purification and drying, the water regain of the spheres was determined in order to classify the molecular sieving capability of the cross-linked polymer. Water regain can be determined by methods well known in the art, and generally involves hydrating 1 gram of dry composition, and determining the amount of water absorbed by the 1 g of the dry composition. Generally, greater swelling capacity relates to larger pores (e.g., less cross-linking) and a higher molecular weight exclusion.

More specifically, a stabilizing agent, such as cellulose acetate butyrate was dissolved in ethylene dichloride at 3% wt/vol and heated to about 50° C. while stirring at about 200 RPM in a 1–2 liter cylindrical reaction vessel. Dextran (MW 40,000) was dissolved in water at 15% wt/vol with 5N NaOH at 2% of the dextran weight. The dextran solution was gradually added to the stabilizing mixture with continued heating and stirring. When droplets of the desired size were formed (30–500 μm), a cross-linking agent such as epichlorohydrin was added to the vessel at 20% of the dextran weight. The reaction formed cross-linked gel spheres in 1–3 hours, but was allowed to proceed up to 16 hours before termination. Acetone was added and decanted twice to remove the stabilizer (cellulose acetate butyrate). The spheres were then treated with NaOH (equal parts of 2N NaOH and 95% ethyl alcohol) for about 15 mins., and neutralized with dilute acid (1N HCl) before filtration and washing with water. The swollen spheres were shrunk with alcohol treatment (25, 50, 75, 100% serial alcohol washes) as described previously. A final alcohol wash contained calcium chloride (0.04–1%). The alcohol was evaporated by drying at about 70° C., thus trapping the calcium in the pores and on the surface of the dextran spheres. The final product was a dry cross-linked dextran-calcium ion composition. The water regain was 20 ml/g.

Example 9

Cotton-Alginate-Dextran Compositions

A pharmaceutically acceptable cotton (cellulose) gauze was immersed in or sprayed with a sodium alginate solution (0.5–4%). The wet sodium alginate coated gauzes were sprayed or dusted with dextran-calcium spheres, prepared as described previously. Calcium exchanged with sodium in the alginate, resulting in cross-linked calcium alginate. Ionic bonds formed between cellulose, alginate, and dextran, thereby chemically incorporating the spheres into the gauze to form the hemostatic compositions.

Example 10

Dextran-Alginate Spheres 43 g dextran (MW 40,000) was dissolved in 50 ml 2N NaOH and mixed with a 50 ml solution of 2% sodium alginate (43% dextran and 1% alginate in 100 ml of 1 N NaOH). 50–200 μm dextran-alginate droplets were linked and cross-linked in a solution of 1.7% calcium chloride. The spheres were further linked and cross-linked by adding 7.2 ml epichlorohydrin to 100 ml of the calcium chloride solution at 45° C. with agitation. The reaction continued for up to 16 hours until the desired amount of linking and cross-linking occurred. The spheres were neutralized with dilute HCl, washed in increasing concentrations of alcohol (25, 50, 75, 100%) and dried at about 70° C. overnight. The water regain was 10 ml/g.

Example 11

Cotton-Dextran-Alginate Sphere Composition

Cross-linked and linked dextran-alginate spheres, prepared as described previously, were washed in a final calcium chloride alcohol wash (0.04–1% calcium chloride). The alcohol was evaporated to trap the calcium in the pores of the spheres. The spheres were then chemically incorporated into gauze containing sodium alginate, as described previously.

Example 12

Compositions Having Dextrans of Different Molecular Weights 100 g of dextran (MW 2,000,000) dissolved in 2000 ml 0.5N NaOH was mixed with 30 g of dextran spheres, prepared as described previously. The cross-linked spheres and dextran solutions were mixed, and 100 g epichlorohydrin added. A pharmaceutically acceptable cellulose gauze was placed in a flat bottomed dish and the alkaline epichlorohydrin/dextran sphere/dextran solution was slowly poured over the gauze to thoroughly coat the fibers with the dextran spheres and dextran solution The coated gauze was heated at 50° C. with gentle rocking, until a gel formed on the gauze fibers, typically in 1–2 hours. The coated gauze was removed from the solution and placed in a flat bottom dish and heating was continued until the desired end-point, approximately 8–12 hours. The gauze was neutralized, washed, and dried, as described previously.

Example 13

Tests of Cotton-Alginate-Dextran Compositions and Calcium-Dextran Spheres

Two different alginates (G, M) were applied in 0.5% and/or 1% concentrations to 12-ply 2×2 cotton gauze squares, Type VII, in either 2 or 4 mL amounts. 0.5 g of calcium-dextran spheres (containing 3, 6, 12, or 24 mM calcium) were ionically bonded to the sodium alginate on the gauze. Freshly drawn human blood was added to each test sample, with 0.5 mls added to each calcium-dextran-alginate gauze and 0.1 ml added to the calcium-dextran spheres alone. Gauze immersed only in sodium alginate was used as a control.

The blood added to the calcium-dextran spheres clotted upon contact. All of the calcium-dextran-alginate gauzes clotted the blood in less than 5 minutes, whereas alginate only gauzes produced weakly clotted blood in >5 mins. See Table 1 below.

TABLE 1

Clotting Times for Hemostatic Compositions

|  | gauze + 4 ml .5% alginate G | gauze + 4 ml 1% alginate G | gauze + 2 ml 1% alginate G | gauze + 4 ml 1% alginate M |
|---|---|---|---|---|
| 0 mM Ca++ control |  | >5 min. | >5 min. | >5 min. | >5 min. |
| 3 mM Ca++ dextran spheres | instantly | not tested | <5 min. | not tested | not tested |
| 6 mM Ca++ dextran spheres | instantly | <5 min. | <5 min. | <5 min. | <5 min. |
| 12 mM Ca++ dextran spheres | instantly | <5 min. | <5 min. | <5 min. | <5 min. |
| 24 mM Ca++ dextran spheres | instantly | <5 min. | <5 min. | <5 min. | <5 min. |

What is claimed is:

1. A bandage consisting essentially of a hemostatic composition, said hemostatic composition comprising cellulose and dextran covalently linked to said cellulose.

2. The bandage of claim 1, wherein said dextran is in the form of covalently cross-linked beads.

3. The bandage of claim 1, wherein the molecular weight of said dextran ranges from about 10,000 to about 2,000,000 Daltons.

4. The bandage of claim 3, wherein the molecular weight of said dextran ranges from about 20,000 to about 100,000 Daltons.

5. The bandage of claim 1, wherein said covalently linked dextran has a molecular weight exclusion limit greater than about 30,000 Daltons.

6. The bandage of claim 1, wherein said cellulose is cotton.

7. The bandage of claim 6, wherein said cellulose is cotton gauze.

8. The bandage of claim 1, further comprising cross-linked alginate linked to said cellulose.

9. The bandage of claim 8, wherein said cross-linked alginate is covalently linked to said cellulose.

10. The bandage of claim 8, wherein said dextran is in the form of covalently cross-linked beads.

11. The bandage of claim 10, wherein said covalently cross-linked dextran beads comprise Ca2+.

12. A bandage comprising a hemostatic composition, said hemostatic composition comprising ionically linked dextran-alginate spheres covalently linked to cellulose.

13. The bandage of claim 12, wherein said ionically linked dextran-alginate spheres are linked ionically with Ca2+.

14. The bandage of claim 13, wherein said ionically linked dextran-alginate spheres are further cross-linked covalently.

* * * * *

UNITED STATES PATENT AND TRADEMARK OFFICE
CERTIFICATE OF CORRECTION

PATENT NO. : 7,101,862 B2  Page 1 of 1
APPLICATION NO. : 10/334864
DATED : September 5, 2006
INVENTOR(S) : Kent C. Cochrum and Susan Jemtrud It is certified that error appears in the above-identified patent and that said Letters Patent is hereby corrected as shown below:

Title Page, Assignee, please delete "Area Laboratories, LLC" and insert --Crosslink-D, Incorporated--therefor;

Title Page, Inventors, Susan Jemtrud, please delete "San Francisco" and insert --Auburn-- therefor;

Column 18, line 26, please delete "consisting essentially of" and insert --comprising-- therefor;

Column 18, line 27, please delete "comprising" and insert --consisting essentially of-- therefor.

Signed and Sealed this

Twenty-seventh Day of February, 2007

JON W. DUDAS
*Director of the United States Patent and Trademark Office*